United States Patent [19]

Thomas, III et al.

[11] Patent Number: 4,921,415

[45] Date of Patent: May 1, 1990

[54] CURE MONITORING APPARATUS HAVING HIGH TEMPERATURE ULTRASONIC TRANSDUCERS

[75] Inventors: Lewis J. Thomas, III, Schenectady; Robert S. Gilmore, Burnt Hills; Homer H. Glascock, II, Scotia, all of N.Y.

[73] Assignee: General Electric Company, Schenectady, N.Y.

[21] Appl. No.: 272,358

[22] Filed: Nov. 15, 1988

Related U.S. Application Data

[62] Division of Ser. No. 126,138, Nov. 27, 1987, Pat. No. 4,825,117.

[51] Int. Cl.⁵ ............................................. B29C 35/02
[52] U.S. Cl. .................................... 425/135; 264/23; 264/40.2; 425/144; 425/149; 425/174.2
[58] Field of Search ............... 425/29, 135, 140, 143, 425/149, 144, 174.2; 264/23, 40.1, 40.2, 40.3; 73/54, 618; 310/346; 228/193; 357/82

[56] References Cited

U.S. PATENT DOCUMENTS

| H465 | 5/1988 | Brown | 73/590 |
|---|---|---|---|
| 2,310,612 | 2/1943 | Bremer et al. | 310/346 X |
| 2,755,662 | 7/1956 | Swengel | 73/54 X |
| 3,187,207 | 6/1965 | Tomes | 310/346 X |
| 3,673,442 | 6/1972 | Sonderegger | 310/346 X |
| 3,735,166 | 5/1973 | Bradley | 310/346 X |
| 4,252,263 | 2/1981 | Houston | 228/193 |
| 4,266,157 | 5/1981 | Peters | 310/346 X |
| 4,366,713 | 1/1983 | Gilmore et al. | 73/618 |
| 4,392,153 | 7/1983 | Glascock, II et al. | 357/82 |
| 4,398,117 | 8/1983 | St. Cyr | 310/346 X |
| 4,430,596 | 2/1984 | Shanley | 310/346 X |
| 4,444,352 | 4/1984 | Glascock, II et al. | 228/193 |
| 4,455,268 | 6/1984 | Hinrichs et al. | 425/143 |
| 4,740,146 | 4/1988 | Angelbeck | 425/174.2 X |
| 4,758,803 | 7/1988 | Thomas, III | 331/65 |
| 4,773,021 | 9/1988 | Harris et al. | 364/476 |
| 4,779,452 | 10/1988 | Cohen-Tenoudji et al. | 73/54 |

OTHER PUBLICATIONS

Conradi, M. S. and Miller, J. G., "A Tansmission Oscillator Ultrasonic Spectrometer", Rev. Sci. Instrum., 45, Mar. 1974, pp. 358-360.

Mallett, L. F., "Microcomputer-Based Control of Composite Curing", M.S. Thesis, MIT, Jun. 1985, pp. 2, 25–48, 150, 151.

Primary Examiner—Richard L. Chiesa
Attorney, Agent, or Firm—Paul R. Webb, II; James C. Davis, Jr.

[57] ABSTRACT

An apparatus for monitoring the curing of a fiber reinforced composite plastic which is cured at temperatures of the order of 350° C. and an ultrasonic transducer assembly useful in the apparatus. The transducer assembly comprises a lithium niobate piezoelectric element having anisotropic coefficients of thermal expansion which is mounted on a metal base of the transducer assembly by means of a layer of structured copper. The structured copper is thermo-compression diffusion bonded to the lithium niobate element and to the metal base, and is compliant in a transverse direction to compensate for differential thermal expansions while affording good electrical and thermal conductivity and good acoustic coupling between the lithium niobate element and metal base.

1 Claim, 2 Drawing Sheets

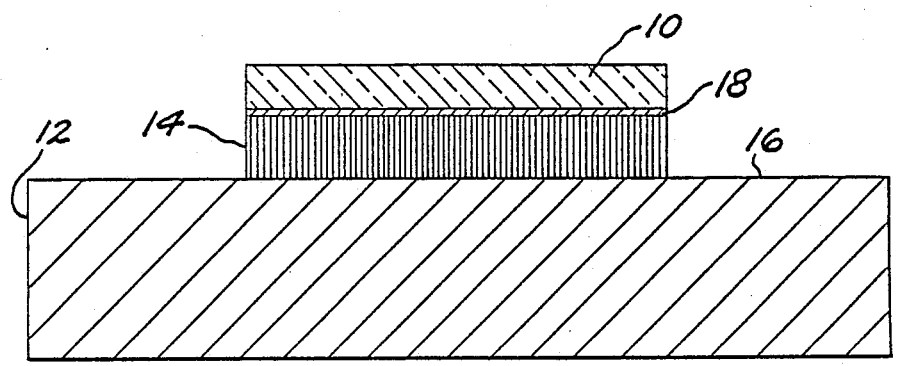
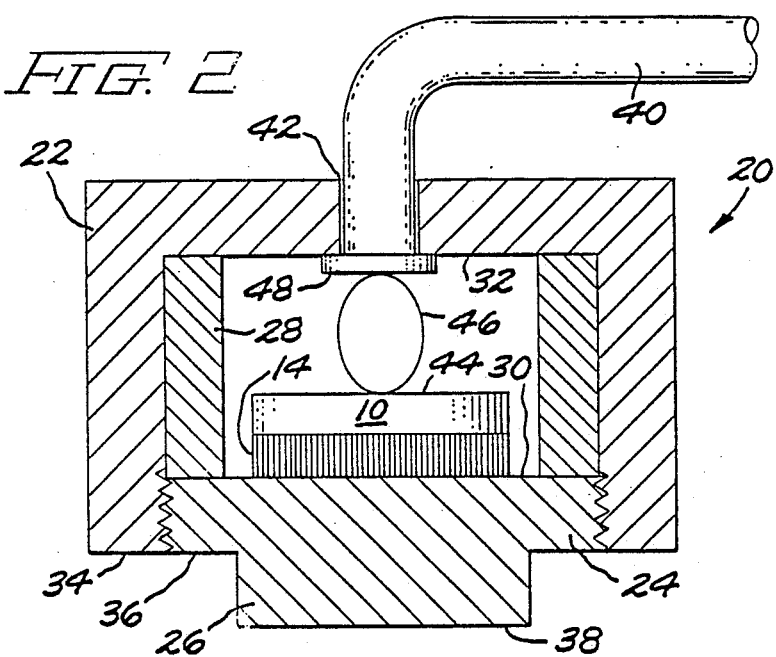

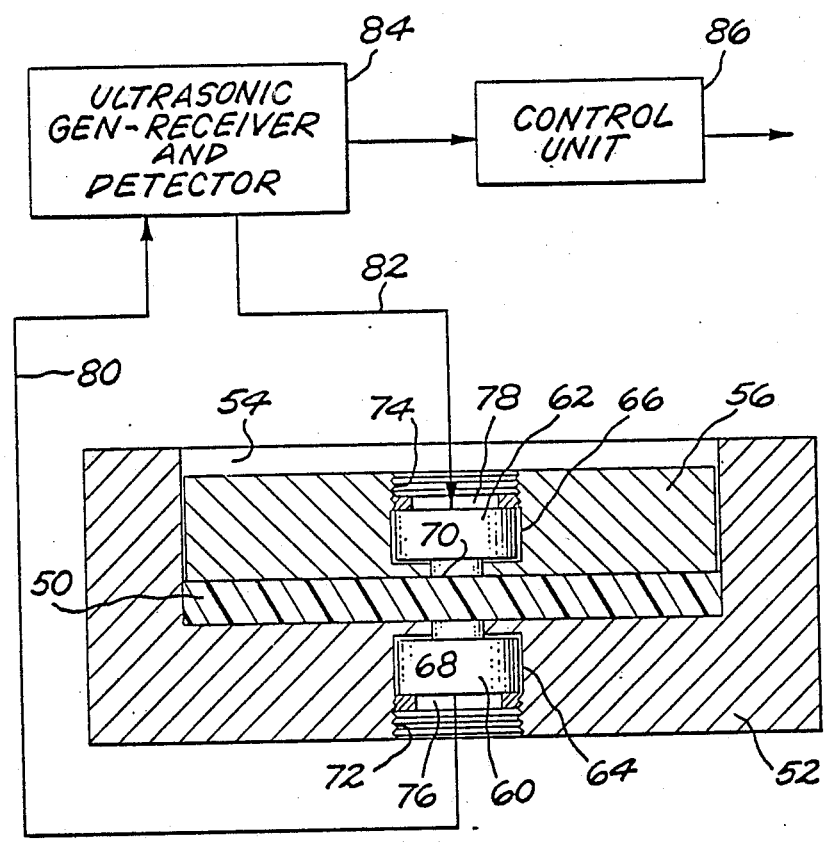

CURE MONITORING APPARATUS HAVING HIGH TEMPERATURE ULTRASONIC TRANSDUCERS

This application is a division of Ser. No. 126,138 filed Nov. 27, 1987, now U.S. Pat. No. 4,825,117.

BACKGROUND OF THE INVENTION

This invention relates to piezoelectric ultrasonic transducers for generating and detecting acoustic energy in high temperature applications.

Piezoelectric materials are convenient for implementing ultrasonic transducers for generating and detecting acoustic energy. Many piezoelectric materials, however, cannot be used in high temperature environments. Lead titanate zirconate (PZT), for example, is a commonly used ferroelectric ceramic which has desirable piezoelectric properties. However, the Curie temperature of PZT ranges from about 200° C. to 350° C., and PZT transducers are generally useful only up to about 150° C. An example of a higher temperature application in which ultrasonic energy may be advantageously employed involves monitoring the curing of composite fiber-reinforced plastics, such as graphite reinforced PMR-15 resin. During the curing of such composite plastics, it is desirable to adjust process parameters such as temperature and pressure in response to the state of the plastic material, which requires a non-invasive technique for determining the degree of cure of the plastic while the cure is in progress. During curing, plastics undergo large changes in elastic moduli, and it has been found that changes in their ultrasonic properties such as the velocity and attenuation of sound through the plastic can provide a measure of its degree of cure.

Commercial composite plastics, such as PMR-15, are typically cured at temperatures of the order of 350° C. At these temperatures, only certain piezoelectric materials are suitable. One such material is lithium niobate ($LiNbO_3$). Lithium niobate has a Curie temperature of 1210° C., which is only 40° C. less than its melting point, and can readily function as a piezoelectric element at 350° C. In order to fabricate an ultrasonic transducer, a piezoelectric element may be bonded onto a metal substrate or base which serves to protect the element from the environment and to couple acoustic energy to and from the element. However, the coefficients of thermal expansion of lithium niobate are quite anisotropic, i.e., vary with crystallographic direction, for the preferred crystal cuts of lithium niobate, which makes it impossible to match the thermal expansion coefficients of a lithium niobate piezoelectric element and its metal substrate. Because of differential thermal expansion, the piezoelectric element is subjected to substantial stress which can cause it to fracture. Bonding the piezoelectric element to its metal substrate in such a manner as to minimize stress on the piezoelectric element due to differential thermal expansion, while maintaining efficient acoustic coupling presents a considerable challenge and is a problem which has heretofore not been satisfactorily solved.

Accordingly, it is desirable to provide a piezoelectric ultrasonic transducer assembly which is useful at high temperatures and which is compensated for differential thermal expansions between the piezoelectric element and its substrate in order to minimize stress on the piezoelectric element, and it is to this end that the present invention is directed.

SUMMARY OF THE INVENTION

In one aspect, the invention provides a temperature compensated ultrasonic transducer assembly which is useful for high temperature applications in which a piezoelectric transducer element is mounted on a metal substrate by means of an intermediate compliant metal layer which functions as a strain buffer to compensate for differences in thermal expansion between the piezoelectric element and the metal substrate. The metal layer is compliant in directions parallel to the surface of the substrate and preferably has substantially no shear modulus in these directions so that it easily accommodates differential thermal expansions while minimizing the stresses applied to the piezoelectric element and affording good acoustic coupling between the piezoelectric element and the metal substrate.

In a preferred form, the compliant layer is a layer of structured copper comprising a bundle of substantially parallel filamentary strands of copper closely packed together at a density of near 90% with the ends of the copper strands diffusion bonded to the piezoelectric element and to the metal substrate. The copper strands efficiently propagate acoustic energy along their lengths and afford good acoustic coupling between the piezoelectric element and the substrate regardless of small shifts due to thermal expansion or contraction. While structured copper is a preferred material for the compliant layer, other structured metals may also be used.

In another aspect, the invention affords a temperature compensated ultrasonic transducer assembly comprising a slab of piezoelectric material which has anisotropic coefficients of thermal expansion. One face of the slab is bonded to a surface of a structured copper layer, and an opposite surface of the structured copper layer is bonded to a metal base. A metal cap is connected to the metal base to form a housing which encloses the slab of piezoelectric material and the structured copper layer, and a resilient member contracts an opposite face of the slab to provide an electrical connection thereto.

In still another aspect, the invention affords apparatus for monitoring a process for curing a composite plastic in which the plastic is cured under pressure and at an elevated temperature in a mold. The apparatus comprises a first transducer assembly for transmitting acoustic energy through the plastic; a second transducer assembly for receiving the acoustic energy transmitted through the plastic; means connected to the first and second transducer assemblies for measuring the velocity and attenuation of the acoustic energy through the plastic to determine the state of cure of the plastic; and means responsive to the measuring means for controlling the pressure and temperature of the curing process. Each transducer assembly comprises a housing having a base in contact with the plastic, and a piezoelectric transducer element within the housing which is mounted on the base by an intermediate compliant layer of structured metal.

BRIEF DESCRIPTION OF THE DRAWINGS

FIG. 1 is an enlarged sectional view illustrating the general form of a transducer assembly in accordance with the invention;

FIG. 2 is a sectional view of a preferred form of a transducer assembly in accordance with the invention which is useful for monitoring the curing of a composite fiber-reinforced plastic; and FIG. 3 is a diagrammatic view of apparatus utilizing the transducer assembly of FIG. 2 for monitoring the curing of a composite fiber-reinforced plastic.

DESCRIPTION OF A PREFERRED EMBODIMENT

The invention provides temperature compensated piezoelectric transducer assemblies which are useful in high temperature environments. Transducer assemblies in accordance with the invention are particularly well adapted for monitoring the curing of composite fiber-reinforced plastics and will be described in that context. However, as will become apparent, this is illustrative of only one utility of the invention.

Piezoelectric ultrasonic transducer assemblies generally comprise a piezoelectric element such as a slab or a wafer of a piezoelectric crystal which is mounted on a metal substrate and contacted by one or more electrodes. The metal substrate may be the base of a housing which encloses the piezoelectric element. The base serves generally to couple acoustic energy between the transducer element and an object or material in contact with the base. For efficient acoustic coupling, the transducer element and the base must be in intimate contact with one another, and it is common to bond the transducer element directly to the base. If the coefficients of thermal expansion of the base metal and the piezoelectric material are not matched, the transducer element will be subjected to stresses caused by differential thermal expansion when the transducer assembly undergoes thermal excursions. Piezoelectric materials are typically weak in tensile strength, and the stresses resulting from thermal mismatch may cause fracturing of the transducer element. The problem is particularly severe for transducer assemblies intended for use at high temperatures since the thermal excursions to which they are subjected are quite high. This problem is further complicated by the fact that the coefficient of thermal expansion of the piezoelectric element may vary in different directions, making it virtually impossible to match the symmetrical thermal expansion coefficient of the base metal.

Lithium niobate is a piezoelectric material which is useful at high temperatures of the order of 350° C. at which commercial composite fiber-reinforced plastics are typically cured. The thermal expansion coefficient of lithium niobate, however, are quite anisotropic. Lithium niobate has a triagonal crystal structure, and has coefficients of thermal expansion relative to the "a" and "c" crystal axes of:

$$\alpha_a = 15.4 \times 10^{-6}/°K.$$

$$\alpha_c = 7.5 \times 10^{-6}/°K.$$

Longitudinal wave transducers may be produced by cutting the lithium niobate crystal either along a plane perpendicular to the c-axis (the axis of symmetry) of the crystal, which is usually referred to as a z-cut, or along a plane parallel to the x-axis of the crystal and at an angle of 36° to the c-axis of the crystal, which is usually referred to as a 36° rotated y-cut. Shear wave transducers may be produced by cutting the crystal either along a plane parallel to the y-axis of the crystal and at an angle of 41° to the c-axis of the crystal, referred to as a 41° rotated x-cut, or along a plane parallel to the x-axis of the crystal and at an angle of 163° to the c-axis, which is referred to as a 163° rotated y-cut.

Although the coefficients of thermal expansion for a z-cut longitudinal wave transducer are isotropic with respect to rotations about an axis perpendicular to the face of the transducer, for longitudinal wave transducers the 36° rotated y-cut is preferred since it offers the most efficient coupling. The coefficients of thermal expansion for this cut, however, are anisotropic. The transverse thermal expansion coefficient, $\alpha_t$, along a direction in the plane of the transducer crystal face and perpendicular to the crystal axis which lies in the plane of the transducer face, may be estimated by assuming it to be equal to a simple vector sum of the anisotropic thermal expansion coefficients. Accordingly, the transverse thermal expansion coefficient may be estimated as:

$$\alpha_t(\theta) = \alpha_c \cos^2(H) + \alpha_a \sin^2(H) \quad (1)$$

where $\theta$ is the angle of the appropriate cut from the c-axis of the crystal. Therefore, for the 36° rotated y-cut, the transverse thermal expansion coefficient obtained from Equation (1) is:

$$\alpha_t(36°) = 10.2 \times 10^{-6}/°K.$$

Perpendicular to this direction, but in the plane of the face of the transducer, the expansion coefficient, as noted above, is:

$$\alpha_a = 15.4 \times 10^{-6}/°K.$$

Unlike longitudinal wave transducers, shear wave transducers cut from a lithium niobate crystal require a rotated cut. Therefore, the thermal expansion coefficients will always be anisotropic with respect to rotations about an axis perpendicular to the face of the transducer element. From Equation (1), the transverse thermal expansion coefficient for the 41° rotated x-cut and the 163° rotated y-cut are, respectively:

$$\alpha_t(41°) = 10.9 \times 10^{-6}/°K.$$

$$\alpha_t(163°) = 8.2 \times 10^{-6}/°K.$$

The 41° rotated x-cut has a value for $\alpha_t$ which is closer to $\alpha_a (15.4 \times 10^{-6}/°K.)$ than the 163° rotated y-cut, and, accordingly, will have thermal expansion coefficients which are less anisotropic than those of the 163° rotated y-cut.

Each of the directional thermal expansion coefficients of lithium niobate may be matched individually reasonably well by any of several different materials. The following Table 1 lists the thermal expansion coefficients of some typical metals.

TABLE 1

| Metal | Thermal Expansion Coefficient ($10^{-6}/°K$) |
|---|---|
| Al | 25 |
| Cu | 16.6 |
| Au | 14.2 |
| Fe | 12 |
| Ni | 13 |
| Ag | 19 |
| Sn | 20 |
| Ti | 8.5 |
| V | 8 |
| Zn | 35 |

From above, the thermal expansion coefficient of lithium niobate in the plane of the face of the transducer element range from $8.2 \times 10^{-6}$/°K. to $15.4 \times 10^{-6}$/°K. As shown in the Table, aluminum, silver, tin, and zinc have thermal expansion coefficients well above the range of lithium niobate, and those of titanium and vanadium are well below this range. Copper, gold, iron, and nickel all exhibit thermal expansion coefficients reasonably close to the range spanned by lithium niobate. However, no isotropic material which expands equally in all directions can match the highly anisotropic thermal expansions of lithium niobate. As a result, differential thermal expansion between the lithium niobate element and its base will inevitably provide stresses. The amount of stress on the lithium niobate element will depend on the thermal mismatch, the temperature range of which the element and base are subjected, and the relative thicknesses of the element and base. If the base is a thin foil, its dimensional changes will be constrained to match those of the element and the stresses exerted on the element will be smaller than for a thicker base. A thin foil base, however, has a number of disadvantages, and in many instances is not practical. Thus, it is desirable to employ a material for the base metal which has a thermal expansion coefficient close to the range spanned by lithium niobate in order to minimize the thermal mismatch between the lithium niobate element and the metal base. Of the above metals, copper is a preferred choice for the base metal. However, the mismatch still produces stress on the lithium niobate element.

In accordance with the invention, the differential thermal expansions between the piezoelectric transducer element and the metal base, are compensated, and stress on the element is minimized by employing an intermediate layer of material between the transducer element and the base which is compliant in the lateral or transverse direction. FIG. 1 illustrates the general form of a transducer assembly in accordance with the invention.

As shown in the figure, a transducer element 10 comprising a thin slab or wafer of piezoelectric material, such as lithium niobate, is mounted on a metal substrate or base 12, as of copper or steel, by means of a compliant intermediate layer 14 of material disposed between the transducer element and the base. Intermediate layer 14 may comprise a layer of structured metal, and preferably comprises a layer of structured copper. As is well known, structured copper comprises a bundle of substantially parallel, equal length, filamentary strands of copper which are closely packed together to a density of the order of 90%. As indicated in FIG. 1, the parallel strands of copper extend between the upper surface 16 of base 12 and transducer element 10. The ends of the copper strands are preferably thermo-compression diffusion bonded to the transducer element and to the base. To facilitate bonding of the structured copper to the piezoelectric material, a thin layer 18 of the order of 1 micron thickness of gold, silver or copper may be deposited, as by sputtering, onto the lower face of the transducer element, as shown in the figure. If base 12 is formed of copper, the structured copper layer may be diffusion bonded directly to the base. For other materials, such as steel, an interface layer of gold, silver or copper such as layer 18 may first be deposited on the surface of the base to facilitate bonding to the structured copper.

A more detailed description of the structured copper member and the thermo-compression diffusion bonding process are given in U.S. Pat. No. 4,252,263 to Houston, U.S. Pat. No. 4,392,153 to Glascock, II et al., and U.S. Pat. No. 4,444,352 to Glascock, II et al., all of which are assigned to the same assignee as the present invention and incorporated by reference herein.

Transducer element 10 may be in the shape of a circular disk with a diameter of the order of 0.6–0.7 inch, for example, The structured copper layer may have the same shape as the transducer element, i.e., a disk, and as indicated in FIG. 1 is preferably dimensioned to match the size of the transducer element. The thickness of the structured copper layer should be selected with regard to the thermal expansion coefficients of the piezoelectric element and base, and with regard to the anticipated temperature of use such that the copper strands have sufficient length to compensate for differential thermal expansions between the piezoelectric element and the base. For a lithium niobate transducer element having a diameter of 0.6–0.7 inch and an expected temperature of 350° C., the structured copper layer may have a thickness of the order of 0.1 inch, for example. The structured copper exhibits substantial structural integrity while still allowing individual movement of the separate strands of copper in a direction parallel to the faces of the layer, i.e., in the transverse direction. This enables the structured copper layer to easily accommodate differential thermal expansions in a transverse plane and affords substantial strain relieving capability. While other metals, such as tungsten or aluminum, for example, may be used for the structured metal layer, copper is advantageous since it affords high thermal and electrical conductivity, as well as efficient coupling of acoustic energy between the transducer element and the base. It is similarly advantageous to use copper for the base since the thermal expansion coefficient of copper is reasonably close to the range of the anisotropic thermal coefficients of lithium niobate. It is not necessary, however, that the thermal expansion coefficients of the transducer element and the base match closely since the structured copper layer can accommodate thermal differential expansion reasonably well, and the base may easily be formed of steel, for example. Because of the substantial strain relieving ability of the compliant structured metal layer, it affords a rugged piezoelectric transducer assembly which can easily accommodate large thermal excursion and multiple thermal cycles without damage to the piezoelectric element.

FIG. 2 illustrates a preferred embodiment of a transducer assembly 20 in accordance with the invention which is particularly well adapted for monitoring the high temperature curing of a composite fiber-reinforced plastic, such as PMR-15. As shown in FIG. 2, transducer assembly 20 may comprise a piezoelectric transducer element 10, as of lithium niobate, enclosed within the interior of a cylindrical housing comprising an annular cap 22 which is threaded onto a stepped-diameter circular base plate 24 having a depending centrally located smaller diameter circular plug portion 26. A hollow cylindrical spacer 28 may be disposed within the housing between the upper surface 30 of the base plate and the underside surface 32 of the top portion of the cap, the spacer preferably being sized so that the bottom 34 of the cap and the lip 36 of the base plate are substantially flush. Cap 22 and base plate 24 may be formed of either steel or copper, and the top and bottom faces 30 and 38, respectively, of the base plate are preferably polished.

Transducer element 10 may be mounted on the top face 30 of the base plate by an intermediate compliant layer 14 of structured metal, such as structured copper, as previously described. The structured copper layer is preferably thermo-compression diffusion bonded to the lower face of the transducer element and to the top face of the base plate. A coaxial cable 40 may enter the housing through an opening 42 in the top of the cap and have its center conductor (not illustrated) electrically connected to the top face 44 of the transducer element by means of a spring contact 46, which in the form illustrated in FIG. 2, may comprise a circular or oval shaped resilient electrically conductive member. A second electrical connection to the opposite lower face of the transducer element is provided through the structured copper layer and the metal housing to the outer shield (also not specifically illustrated) of the coaxial cable. For this purpose, the shield of the coaxial cable 40 is soldered to cap 22 by a conventional high temperature solder at opening 42. Ceramic washer 48 insulates the center conductor of the coaxial cable from cap 22.

The housing of transducer assembly 20 serves to protect the transducer element from the environment. It is not necessary that the housing be constructed in the manner illustrated in FIG. 2, and the housing may take any other convenient form or shape.

FIG. 3 illustrates an apparatus in accordance with the invention for monitoring the curing of a composite fiber-reinforced plastic. As shown in the Figure, the plastic 50 may be cured in a two-part steel mold comprising a lower mold body 52 having a cavity 54 into which the plastic 50 is placed, and an upper mold ram member 56 which slides within the cavity of the mold body to exert pressure on the plastic. The mold may be placed between upper and lower heated platens (not illustrated) of a conventional hot press which respectively contact ram 56 and body 52. The heated platens of the press exert a controlled pressing force on the ram and body to exert a predetermined pressure on the plastic during curing, and the temperature of the platens is controlled to transfer a predetermined amount of heat to the plastic by conduction through the mold members. The temperature and pressure applied to the plastic are typically varied as a function of time during a curing cycle in accordance with empirically determined schedule for the particular plastic being cured. Because of the variations in the plastic material itself and/or variations in the curing process, the empirically determined schedule does not always result in optimum curing. Optimum curing requires that the press be controlled to adjust the temperature and pressure during a curing cycle in response to the state of material during the curing process. This requires a non-invasive technique for monitoring the degree of cure of the plastic during the curing process. The apparatus of FIG. 3 affords such a non-invasive technique by enabling changes in the ultrasonic properties, such as the velocity and attenuation of sound through the plastic, to be monitored continuously throughout the curing cycle. The changes in the ultrasonic properties of the plastic provide a sensitive and reliable measure of its degree of cure and permit on line control of the press to optimize the curing process.

As shown in FIG. 3, a pair of transducer assemblies 60 and 62, each of which may be similar to the transducer assembly illustrated in FIG. 2, may be incorporated into body 52 and ram 56, respectively, of the curing mold as shown in FIG. 3. For this purpose, the mold body and the mold ram may be provided with stepped-diameter openings 64 and 66, respectively, which are sized to receive the transducer assemblies and to position the bottom faces 68 and 70 of the plug portions of the base plates of the transducer assemblies flush with the interior surfaces of the mold members and in contact with the plastic. The outer portions of the two openings 64 and 66 may be threaded, as shown at 72 and 74, respectively, and the transducer assemblies 60 and 62 may be held in fixed position within the openings by corresponding threaded rings 76 and 78.

Transducer assemblies 60 and 62 may be connected by lines 80 and 82, respectively, to a conventional ultrasonic generator-receiver and detector 84. One of the transducer assemblies, for example 62, is employed as a transmitter for generating acoustic energy and for transmitting the acoustic energy through the curing plastic 50. The other transducer assembly 60 is employed as a receiver for receiving the acoustic energy after it has propagated through the plastic and for providing a corresponding signal via line 80 to the ultrasonic generator-receiver and detector unit 84. The generator-receiver and detector unit may supply output signals representative of one or more of the ultrasonic properties of the plastic, such as the velocity and attenuation of the acoustic energy through the plastic, to a control unit 86. The control unit, which may comprise a computer, may utilize the signals from the generator-receiver and detector unit 84 to determine the state of cure of the plastic, and output appropriate signals to the press for optimizing the curing.

Since many commercial composite plastics are cured at temperatures of the order of 350° C., the piezoelectric elements of transducer assemblies 60 and 62 must be capable of operating at such temperatures. Moreover, the transducer assemblies are subjected to large temperature excursions (from room temperature up to at least the curing temperature of the plastic) and, accordingly, undergo significant thermal expansion. The compliant structured copper layers of the transducer assemblies relieve the strain which otherwise would be exerted on the piezoelectric elements because of differential thermal expansions, as previously described, and they afford a transducer which is capable of withstanding multiple thermal cycles without damage.

For monitoring the curing of composite plastic, each transducer assembly may employ a 36° rotated y-cut longitudinal wave lithium niobate piezoelectric element. A longitudinal wave piezoelectric element is desirable since during at least a portion of the cure cycle the plastic material is in a liquid state. As the plastic solidifies and hardens, a shear wave transducer may be more sensitive to the cure state of the material. Accordingly, it may be desirable to use both longitudinal wave and shear wave transducers during different portions of the curing cycle for monitoring the curing process. If desired, the transducer assembly of FIG. 2 may be formed to incorporate both longitudinal wave and shear wave piezoelectric elements. Alternatively, separate transducer assemblies, one employing a longitudinal wave element and one employing a shear wave element may be incorporated into each of the mold members 52 and 56 and utilized at different times during the curing cycle.

While a preferred embodiment of the invention has been shown and described, it will be apparent to those skilled in the art that changes can be made in this embodiment without departing from the principles and spirit of the invention, the scope of which is defined in the appended claims.

What is claimed is:

1. Apparatus for monitoring a process for curing a composite plastic in which the plastic is cured under pressure and at an elevated temperature in a mold, comprising a mold, a first transducer assembly secured to the mold for transmitting acoustic energy through the plastic; a second transducer assembly secured to the mold receiving the acoustic energy transmitted through the plastic; means connected to the first and second transducer assemblies of measuring the velocity and attenuation of the acoustic energy through the plastic to determine the state of cure of the plastic; and means responsive to the measuring means for controlling the pressure and temperature of the curing process; each transducer assembly comprising a housing having a cylindrical hollow annular cap and a stepped-diameter annular base threaded to the cap for contact with the plastic in the mold; and a piezoelectric transducer element within the housing, the transducer element being mounted on the base by an intermediate compliant layer of structured metal;

said first and second transducer assemblies being respectively disposed in first and second parts of said mold with the bases of the transducer elements flush with surfaces of the mold parts which contact and press the plastic therebetween;

each base including a projecting portion with a smaller diameter than the housing, the projecting portion contacting the plastic, and wherein the transducer assemblies are received within stepped-diameter holes in the mold parts and fixed in position by threaded rings.

* * * * *